United States Patent
Orr

(10) Patent No.: US 10,159,815 B2
(45) Date of Patent: Dec. 25, 2018

(54) SYSTEM AND METHOD FOR DETECTION OF OXYGEN DELIVERY FAILURE

(71) Applicant: Dynasthetics, LLC, Salt Lake City, UT (US)

(72) Inventor: Joseph Orr, Salt Lake City, UT (US)

(73) Assignee: Dynasthetics, LLC, Salt Lake City, UT (US)

( * ) Notice: Subject to any disclaimer, the term of this patent is extended or adjusted under 35 U.S.C. 154(b) by 950 days.

(21) Appl. No.: 14/569,621

(22) Filed: Dec. 12, 2014

(65) Prior Publication Data

US 2016/0166796 A1     Jun. 16, 2016

(51) Int. Cl.
*A61M 16/10* (2006.01)
*A61B 5/08* (2006.01)
(Continued)

(52) U.S. Cl.
CPC ....... *A61M 16/1005* (2014.02); *A61B 5/0826* (2013.01); *A61B 5/0833* (2013.01); *A61B 5/4839* (2013.01); *A61M 16/0003* (2014.02); *A61M 16/0051* (2013.01); *A61M 16/024* (2017.08); *A61M 16/0672* (2014.02); *A61M 16/0677* (2014.02); *A61M 16/201* (2014.02); *A61B 5/4848* (2013.01); *A61M 2016/003* (2013.01); *A61M 2016/0027* (2013.01); *A61M 2016/0039* (2013.01);
(Continued)

(58) Field of Classification Search
CPC .. A62B 7/00; A62B 7/10; A62B 18/02; A62B 18/025; A62B 23/00; A62B 23/02; A62B 23/025; A62B 23/04; A62B 23/06; A61B 5/0826; A61M 16/1005
See application file for complete search history.

(56) References Cited

U.S. PATENT DOCUMENTS 4,686,975 A    8/1987   Naimon et al.
4,938,212 A    7/1990   Snook et al.
(Continued)

FOREIGN PATENT DOCUMENTS

JP    2007303480    11/2009
WO    01/18500 A1    3/2001
(Continued)

OTHER PUBLICATIONS

International Search Report and Written Opinion of the International Searching Authority, dated Mar. 7, 2016.
(Continued)

*Primary Examiner* — LaToya M Louis
(74) *Attorney, Agent, or Firm* — Durham Jones & Pinegar; Sarah W. Matthews; Christopher Wight

(57) ABSTRACT

A method and apparatus to identify the source of oxygen delivery failure to a patient. The apparatus may include a pressure sensor to detect a patient's breathing pressure and ambient pressure, an oxygen flow analyzer to measure oxygen flow to the patient, and a processor to analyze the breathing pressure values, ambient pressure value, and oxygen flow rate values. When the oxygen flow rate value is greater than a predetermined threshold value, the processor is programmed to compare the breathing pressure values to the ambient pressure value and output an apnea alarm or an oxygen delivery device displacement alarm.

19 Claims, 9 Drawing Sheets

(51) Int. Cl.
*A61M 16/00* (2006.01)
*A61M 16/06* (2006.01)
*A61M 16/20* (2006.01)
*A61B 5/083* (2006.01)
*A61B 5/00* (2006.01)

(52) U.S. Cl.
CPC ............... *A61M 2016/102* (2013.01); *A61M 2202/0208* (2013.01); *A61M 2205/18* (2013.01); *A61M 2205/3334* (2013.01); *A61M 2205/3358* (2013.01); *A61M 2205/502* (2013.01); *A61M 2205/581* (2013.01); *A61M 2205/583* (2013.01); *A61M 2205/70* (2013.01); *A61M 2230/40* (2013.01)

(56) References Cited

U.S. PATENT DOCUMENTS

| | | | |
|---|---|---|---|
| 5,038,771 | A | 8/1991 | Dietz |
| 5,626,131 | A | 5/1997 | Chua et al. |
| 5,865,174 | A | 2/1999 | Kloeppel |
| 6,544,192 | B2 | 4/2003 | Starr et al. |
| 6,938,619 | B1 | 9/2005 | Hickle |
| 7,007,692 | B2 | 3/2006 | Aylsworth et al. |
| 7,013,898 | B2 | 3/2006 | Rashad et al. |
| 7,066,180 | B2 | 6/2006 | Aylsworth et al. |
| 7,152,604 | B2 | 12/2006 | Hickle et al. |
| 7,213,594 | B2 | 5/2007 | Aylsworth et al. |
| 7,668,579 | B2 | 2/2010 | Lynn |
| 8,475,369 | B2 | 7/2013 | Boatner et al. |
| 9,295,797 | B2 * | 3/2016 | Shissler ............... A61B 5/0826 |
| 2002/0096174 | A1 | 7/2002 | Hill et al. |
| 2002/0195105 | A1 * | 12/2002 | Blue ...................... A61M 16/00 128/204.21 |
| 2008/0072902 | A1 * | 3/2008 | Setzer ............... A61M 16/0051 128/204.21 |
| 2009/0199855 | A1 | 8/2009 | Davenport |
| 2009/0299158 | A1 | 12/2009 | Boatner et al. |
| 2010/0292544 | A1 * | 11/2010 | Sherman ............. A61M 16/024 600/300 |
| 2011/0201956 | A1 | 8/2011 | Alferness |
| 2012/0118291 | A1 | 5/2012 | Brodkin et al. |
| 2012/0203127 | A1 | 8/2012 | Hadas |
| 2013/0152933 | A1 | 6/2013 | Lischer et al. |
| 2013/0239960 | A1 * | 9/2013 | Bertinetti .......... A61M 16/0066 128/202.22 |
| 2014/0030155 | A1 | 11/2014 | Brewer |
| 2014/0330155 | A1 * | 11/2014 | Brewer ............... A61M 16/024 600/532 |
| 2014/0360497 | A1 | 12/2014 | Jafari et al. |
| 2016/0016679 | A1 | 6/2016 | Orr |

FOREIGN PATENT DOCUMENTS

| | | |
|---|---|---|
| WO | 2012098305 A1 | 7/2012 |
| WO | 2014106696 A1 | 7/2014 |

OTHER PUBLICATIONS

International Preliminary Report on Patentability, and Written Opinion of the International Searching Authority from related application PCT/US2015/066998 dated Jun. 22, 2017.

Guyatt AR, Parker SP, McBride MJ. Am J Respir. Crit Care Med. Aug. 1, 2002;166(3):386-91. Measurement of human nasal ventilation using an oxygen cannula as a pitot tube.

Heitman SJ, Atkar RS, Hajduk EA, Wanner RA, Flemons WW. Am Rev Respir Dis. Sep. 1982;126(3):434-8. Validation of nasal pressure for the identification of apneas/hypopneas during sleep.

Montserrat JM, Farré R. Breathing flow disturbances during sleep: can they be accurately assessed by nasal prongs? Am J RespirCrit Care Med. Aug. 1, 2002;166(3):259-60.

Kohler M, Thurnheer R, Bloch KE.Side-selective, unobtrusive monitoring of nasal airflow and conductance. J ApplPhysiol (1985). Dec. 2006;101(6):1760-5. Epub Jul. 13, 2006.

Thurnheer R, Xie X, Bloch KE. Accuracy of nasal cannula pressure recordings for assessment of ventilation during sleep. Am J RespirCrit Care Med. Nov. 15, 2001;164(10 Pt 1):1914-9.

Montserrat JM, Farré R, Ballester E, Felez MA, Pastó M, Navajas D. Evaluation of nasal prongs for estimating nasal flow.

Farré R, Rigau J, Montserrat JM, Ballester E, Navajas D. Am J RespirCrit Care Med. Feb. 2001;163(2):494-7. Relevance of linearizing nasal prongs for assessing hypopneas and flow limitation during sleep.

Ballester E, Badia JR, Hernandez L, Farré R, Navajas D, Montserrat JM. Nasal prongs in the detection of sleep-related disordered breathing in the sleep apnoea/hypopnoea syndrome. EurRespir J. Apr. 1998;11(4):880-3.

International Search Report and Written Opinion of the International Searching Authority from related PCT application No. PCT/US2015/064998, dated Mar. 17, 2016.

International Search Report of PCT/FR2013/052506, dated Jan. 22, 2014.

* cited by examiner

SYSTEM AND METHOD FOR DETECTION OF OXYGEN DELIVERY FAILURE

FIELD OF INVENTION

This invention relates generally to breathing detection systems and methods. It is particularly directed to a system and method for differentiating between a true apnea and displacement of an oxygen delivery device, and calculating a volume of delivered oxygen that is inhaled by a patient.

BACKGROUND

Inadequate ventilation may be one cause of hazards during procedural sedation. Apnea, or lack of respiration, can be caused by the drugs that the patient receives through the intravenous port during sedation. Central apnea occurs when the patient makes no effort or little effort to breathe and is often caused by giving too much opioid agent to the patient. Obstructive apnea occurs when the airway tissues are so relaxed that they block gas flow, thereby reducing the volume of air that the patient receives. Obstructive apnea during sedation is often caused by giving too much sedative agent to the patient. Respiration is usually monitored during sedation using a pulse oximeter that measures the oxygen saturation in the patient's arterial blood. Respiration rate is usually monitored during sedation using transthoracic bioimpedance or capnometry. Transthoracic bioimpedance measures the change in electrical impedance across the chest using the EKG electrodes, and is often unreliable. Additionally, transthoracic bioimpedance cannot detect airway obstruction since the patient's chest still moves during an attempt to force gas through an obstructed airway.

Capnometry measures the concentration of carbon dioxide in the exhaled air and calculates a breath rate by measuring the time between excursions in the carbon dioxide signal. Capnometry is expensive and is known in the field to detect breath attempts as true breaths. Because capnometry does not measure the total volume of exhaled carbon dioxide, only a small volume of exhaled carbon dioxide is needed to cause a detection of a true breath. An additional limitation of capnometry is that the signal is degraded when high oxygen flow is given. This is a challenge because when a patient is hypoxic, the oxygen flow is often increased; however increased oxygen flow dilutes the exhaled carbon dioxide, thereby diminishing the clinician's ability to monitor respiration in the patients that have a great need to be monitored.

Additionally, there is a clinical controversy regarding the use of oxygen during sedation. While some believe oxygen is beneficial, others have stated that addition of oxygen is detrimental because it allows use of excess opioid and sedatives and that added oxygen only delays detection of inadequate respiration by the pulse oximeter.

While oxygen is delivered clinically at fixed flow rate that runs continuously, most of the oxygen delivered is not actually inhaled by the patient. The majority of the supplemental oxygen is wasted as the patient is breathing out (exhaling). Furthermore, even when the patient is inhaling, there is only a brief time when the patient is inhaling with sufficient rate to take in all of the oxygen that is being delivered through the nasal cannula or mask. It may be helpful clinically to calculate the fraction of the supplemental oxygen that actually enters the patient's airways.

Consequently, there is a long felt need for a technology that could more accurately detect a patient's breathing, especially in patients receiving opioids and sedatives. This technology would desirably further differentiate between a true apnea and mere displacement of an oxygen delivery device. It may also be desirable to be able to determine how much of the oxygen delivered to the patient is being inhaled by the patient.

SUMMARY OF THE INVENTION

This present disclosure relates to methods and systems for identifying the source of oxygen delivery failure to a patient. In one aspect, the method may comprise:

detecting a patient's breathing pressure value to determine a plurality of breathing pressure values;

measuring an oxygen flow rate through an oxygen delivery device to provide an oxygen flow rate value;

measuring an ambient pressure to provide an ambient pressure value;

receiving the plurality of breathing pressure values, the oxygen flow rate value, and the ambient pressure value at at least one processor;

the at least one processor analyzing the plurality of breathing pressure values to determine if a patient is breathing or not breathing, and when the processor determines the patient is not breathing and the oxygen flow rate value is greater than a predetermined threshold value, the processor further comparing the plurality of breathing pressure values to the ambient pressure value; and wherein the processor outputs an apnea alarm when the plurality of breathing pressure values is greater than the ambient pressure value, and wherein the processor outputs an oxygen delivery device displacement alarm when the plurality of breathing pressure values is equal to the ambient pressure value.

According to one aspect, the step of measuring an oxygen flow rate through an oxygen delivery device comprises measuring the oxygen flow rate with a differential-type pressure analyzer. According to a different configuration, the step of measuring an oxygen flow rate through an oxygen delivery device comprises measuring the oxygen flow rate with a heated wire, or heated film-type anemometer.

According to another aspect, a pressure sensing device with a solenoid valve may perform the steps of detecting a patient's breathing pressure and measuring an ambient pressure are performed by a pressure sensing device provided with a solenoid valve. The step of measuring an ambient pressure may comprise opening the solenoid valve on the pressure sensing device to ambient pressure.

In some aspects, the processor may output an audible alarm for the apnea alarm and the oxygen delivery device displacement alarm. In another configuration, the processor may output a visual alarm for the apnea alarm and the oxygen delivery device displacement alarm. In one configuration, the predetermined threshold of the oxygen flow rate may be 0.5 liters per minute.

According to some aspects, the step of detecting a patient's breathing pressure value to determine a plurality of breathing pressure values comprises detecting a patient's breathing pressure value for a predetermined amount of time. In another aspect, the method comprises medical personnel selecting a predetermined amount of time.

According to another aspect, the at least one processor comprises an oxygen flow analyzer processor, and a second processor, the oxygen flow analyzer processor in communication with the oxygen flow analyzer and the second processor. In another aspect, the at least one processor comprises a pressure sensor processor, and a second processor, the pressure sensor processor in communication with the pressure sensor and the second processor. And in yet another aspect, the at least one processor comprises an oxygen flow analyzer processor, a pressure sensor processor, and a third processor; the oxygen flow analyzer processor in communication with the oxygen flow analyzer and the third processor, and the pressure sensor processor in communication with the pressure sensor and the third processor.

According to another aspect, the processor may calculate a volume of oxygen inhaled by a patient during at least one predetermined time period. The steps may include the processor:

calculating a K-factor based on the oxygen flow rate value and the plurality of breathing pressure values, and calculating a portion of the breathing pressure value due to a patient's breathing flow to determine a patient breathing flow value, analyzing breathing pressure values to classify each as inhalation or expiration, and for each breathing pressure value classified as inhalation, comparing the patient breathing flow value to the oxygen flow rate value, and when the patient breathing flow value is greater than the oxygen flow rate value, calculating the volume of oxygen due to the oxygen flow rate during the at least one predetermined time period as the volume of inhaled oxygen, and when the patient's breathing flow value is less than the oxygen flow rate value, calculating the volume of oxygen due to the patient breathing flow rate during the at least one predetermined time period as the volume of inhaled oxygen.

According to another aspect, an apparatus is described for identifying the source of oxygen delivery failure to a patient. The apparatus may comprise:

a pressure sensor to detect a patient's breathing pressure and provide a plurality of breathing pressure values, and to measure ambient pressure and provide an ambient pressure value, the pressure sensor in communication with a processor;

an oxygen flow analyzer to measure a parameter indicative of oxygen flow rate through an oxygen delivery device and provide an oxygen flow rate value, the oxygen flow analyzer in communication with the processor;

the processor programmed to receive the plurality of breathing pressure values, the ambient pressure value, and the oxygen flow rate value;

the processor programmed to analyze the plurality of breathing pressure values to determine if a patient is breathing or not breathing, and the processor further programmed to compare the plurality of breathing pressure values to the ambient pressure value when the processor determines the patient is not breathing and the oxygen flow rate value is greater than a predetermined threshold value; and the processor programmed to output an apnea alarm if the plurality of breathing pressure values is greater than the ambient pressure value, and the processor programmed to output an oxygen delivery device displacement alarm when the breathing pressure differential value is equal to the ambient pressure value.

In one configuration, the oxygen flow analyzer comprises a differential-type oxygen flow analyzer. In another configuration, the oxygen flow analyzer comprises a heated wire-type anemometer.

In some configurations, the pressure sensor may be communication with a solenoid valve to switch the pressure sensor between measuring the patient breathing pressure and measuring ambient pressure. The predetermined threshold value of the oxygen flow rate value may be, for example, 0.5 liters per minute.

According to one aspect, the apnea alarm and the oxygen delivery device alarm comprise an audible alarm. According to another aspect, the apnea alarm and the oxygen delivery device displacement alarm comprise a visual alarm.

According to another aspect, an apparatus to deliver a variable flow of oxygen to a patient is provided. The apparatus may comprise:

a flow control valve to deliver a flow of oxygen through an oxygen delivery device;

a pressure sensor to detect the patient's breathing pressure and provide a plurality of breathing pressure values, and to measure ambient pressure and provide an ambient pressure value, the pressure sensor in communication with a processor;

the processor programmed to receive the plurality of breathing pressure values and the ambient pressure value;

the processor programmed to analyze the plurality of breathing pressure values to determine if a patient is breathing or not breathing, and the processor further programmed to calculate an amount of oxygen to deliver to a patient during a predetermined time frame, the amount of oxygen to deliver to the patient being calculated by a pre-selected oxygen flow rate plus an oxygen backlog; and the processor programmed to open the flow control valve when the processor determines the patient is breathing in (inhaling) and the oxygen backlog is greater than zero.

The apparatus may further include an oxygen flow analyzer to measure a parameter indicative of oxygen flow rate through the oxygen delivery device and provide an oxygen flow rate value, the processor programmed to received the oxygen flow rate value. According to one aspect, the processor may be programmed to increment the oxygen backlog during the predetermined time frame by the pre-selected oxygen flow rate multiplied by the predetermined time frame. The processor may be further programmed to decrement the oxygen backlog during the predetermined time frame when the processor determines the patient is breathing, such as the processor decrementing the oxygen backlog by the oxygen flow rate value multiplied by the breathing pressure value.

In one configuration, the flow control valve may include a proportional valve, and the processor may be programmed to send a current input to the solenoid when the processor determines the patient is breathing. The processor may calculate the current input to send to the solenoid by comparing the breathing pressure value to the oxygen backlog, and sending the current input based on the smaller of the breathing pressure value and the oxygen backlog.

According to yet another aspect, there is provided a method for delivering a variable flow of oxygen to a patient. The method may comprise:

detecting a patient's breathing pressure value to determine a breathing pressure value;

receiving the breathing pressure value at least one processor;

the at least one processor incrementing the total amount of oxygen to be delivered based on a pre-selected oxygen flow rate and a predetermined time interval;

the at least one processor analyzing the breathing pressure value to determine if the patient is inhaling or exhaling, and when the processor determines the patient is inhaling, the at least one processor calculating an optimal oxygen flow rate based on the total amount of oxygen to be delivered and the breathing pressure value;

the at least one processor sending a signal to a flow control valve to open the valve sufficiently to deliver the optimal oxygen flow rate;

measuring an oxygen flow rate through an oxygen delivery device to provide an oxygen flow rate value;

receiving the oxygen flow rate value at the least one processor; and the at least one processor decrementing the total amount of oxygen to be delivered based on the oxygen flow rate value.

According to one aspect, the step of the at least one processor incrementing the total amount of oxygen to be delivered may comprise the at least one processor multiplying the pre-selected oxygen flow rate by the predetermined time interval. The step of the at least one processor analyzing the breathing pressure value to determine if the patient is inhaling or exhaling may comprise the at least one processor analyzing the breathing pressure value to determine if it is negative or not negative, and the at least one processor assuming a negative breathing pressure value is due to an inhalation. The step of the at least one processor decrementing the total amount of oxygen to be delivered based on the oxygen flow rate value may include the at least one processor multiplying the oxygen flow rate value by the predetermined time interval to calculate a calculated volume of oxygen delivered, and the at least one processor decrementing the total amount of oxygen to be delivered by the calculated volume of oxygen delivered.

According to another aspect, there is provided a method for identifying a source of oxygen delivery failure to a patient. The method may comprise the steps of:

detecting a patient's breathing pressure value to determine a plurality of breathing pressure values, and receiving the plurality of breathing pressure values at least one processor;

the at least one processor analyzing the plurality of breathing pressure values to determine if the patient is breathing or not breathing, and when the processor determines the patient is not breathing, the processor communicating with a flow valve to deliver a high-flow pulse of oxygen;

measuring an oxygen flow rate through an oxygen delivery device to provide an oxygen flow rate value;

receiving the oxygen flow rate value at the least one processor;

the processor analyzing the oxygen flow rate value, and wherein the processor outputs an insufficient oxygen flow alarm when the oxygen flow rate is not greater than a predetermined threshold value;

measuring a post-oxygen pulse breathing pressure value when the oxygen flow rate is less than the predetermined threshold value;

receiving the post-oxygen pulse breathing pressure value at the at least one processor;

the processor analyzing the post-oxygen pulse breathing pressure value, and wherein the processor outputs an apnea alarm when the post-oxygen pulse breathing pressure value is more negative than a predetermined threshold post-oxygen pulse breathing pressure value, and wherein the processor outputs an oxygen delivery device displacement alarm when the post-oxygen pulse breathing pressure values is equal to or less negative than predetermined threshold post-oxygen pulse breathing pressure value.

According to one aspect, the step of measuring the oxygen flow rate through the oxygen delivery device may include measuring the oxygen flow rate with a differential-type oxygen flow analyzer. In some configurations, the step of measuring the oxygen flow rate through the oxygen delivery device may include measuring the oxygen flow rate with a heated wire-type anemometer. The steps of the processor outputting the apnea alarm and the oxygen delivery device displacement alarm may include outputting an audible alarm and/or a visual alarm. In one configuration, the high-flow pulse of oxygen is between 5 and 15 liters per minute. The predetermined threshold value may between 3 and 7 liters per minute in one configuration, and the predetermined threshold post-oxygen pulse breathing pressure value may be $-0.1$ cm $H_2O$.

According to one configuration, the at least one processor could be an oxygen flow analyzer processor and a second processor, the oxygen flow analyzer processor in communication with the oxygen flow analyzer and the second processor. In another configuration, the at least one processor could be a pressure sensor processor and a second processor, the pressure sensor processor in communication with the pressure sensor and the second processor. In yet another configuration, the at least one processor could be an oxygen flow analyzer processor, a pressure sensor processor, and a third processor; the oxygen flow analyzer processor in communication with the oxygen flow analyzer and the third processor, and the pressure sensor processor in communication with the pressure sensor and the third processor.

According to another aspect, the method may further comprise the processor calculating a volume of oxygen inhaled by the patient during at least one predetermined time period, the processor analyzing the plurality of breathing pressure values to classify each as inhalation or expiration, and for a breathing pressure value classified as inhalation, calculating the volume of inhaled oxygen as the volume of oxygen due to the oxygen flow rate during the at least one predetermined time period.

According to another aspect, there is provided an apparatus for identifying a source of oxygen delivery failure to a patient. The apparatus may include:

a pressure sensor to detect a patient's breathing pressure and provide a plurality of breathing pressure values, and provide a post-oxygen pulse breathing pressure value, the pressure sensor in communication with a processor;

a variable flow valve to deliver a high-flow pulse of oxygen, the variable flow valve in communication with the processor;

an oxygen flow analyzer to measure a parameter indicative of oxygen flow rate through an oxygen delivery device and provide an oxygen flow rate value, the oxygen flow analyzer in communication with the processor;

the processor programmed to receive the plurality of breathing pressure values and to analyze the plurality of breathing pressure values to determine if the patient is breathing or not breathing, and the processor programmed to send a signal to the variable flow valve to open the valve to deliver the high-flow pulse of oxygen when the processor determines the patient is not breathing; and the processor programmed to receive the oxygen flow rate value and analyze the oxygen flow rate value to determine if the oxygen flow rate value is above a predetermined threshold value, and the processor further programmed to output an insufficient oxygen flow alarm when the oxygen flow rate value is below the predetermined threshold value;

the processor programmed to receive the post-oxygen pulse breathing pressure value and analyze the post-oxygen pulse breathing pressure value to determine if the post-oxygen pulse breathing pressure value is more negative than a predetermined threshold post-oxygen pulse breathing pressure value; and the processor programmed to output an apnea alarm if the post-oxygen pulse breathing pressure value is more negative than the predetermined threshold post-oxygen pulse breathing pressure value, and the processor programmed to output an oxygen delivery device displacement alarm when the post-oxygen pulse breathing pressure value is not more negative than the predetermined threshold post-oxygen pulse breathing pressure value.

In one configuration, the oxygen flow analyzer comprises a differential-type oxygen flow analyzer. In another configuration, the oxygen flow analyzer comprises a heated wire, or heated film-type anemometer. The variable flow valve could be a proportional control valve. Depending on the configuration, different values may be used for the high-flow pulse of oxygen, and in one configuration, the pulse may be 5 to 15 liters per minute. The predetermined threshold value of the oxygen flow rate value may be 4 to 10 liters per minute.

In some configurations, the apnea alarm and the oxygen delivery device displacement alarm may include an audible and/or visual alarm.

BRIEF DESCRIPTION OF THE DRAWINGS

The following drawings illustrate what are currently considered to be specific configurations for carrying out the invention.

DETAILED DESCRIPTION

Reference will now be made to the drawings in which the various elements of the illustrated configurations will be given numerical designations and in which the invention will be discussed so as to enable one skilled in the art to make and use the invention. It is to be understood that the following description is only exemplary of the principles of the present invention, and should not be viewed as narrowing the claims which follow.

Definitions

The term "oxygen delivery failure" means the patient is failing to receive oxygen. The threshold for oxygen delivery failure could be set by a clinician, for example, failure to receive a minimum fraction of the set oxygen delivery rate, such as 50% of the oxygen delivery rate. This cause of the oxygen delivery failure could be a failure of the oxygen delivery device, such as if the oxygen delivery device is displaced or if the oxygen supply is insufficient. Oxygen delivery failure could also be caused by a patient's apnea, or failure to breath.

The term "breathing pressure" means the pressure that is sensed by the pressure sensor. This pressure is typically primarily caused by a patient's breathing, with inhalations detected as a negative pressure and exhalations detected as a positive pressure. Breathing pressure can also be caused by the flow of oxygen in an oxygen delivery device, and/or by the ambient pressure.

The term "logic" means an algorithm or a step-by-step method of solving a problem or making decisions. For clarity, the logic herein has been generally shown and described in a step-by-step manner with a particular order. However, the particular order shown is illustrative and not limiting. Some of the steps of the logic shown may be performed in the particular order shown, or some of the steps may be performed in a different order, or some of the steps may be performed at the same time.

The term "processor" means a standard processor, typically equipped with a control unit, a logic unit, and a register.

Figure 1:
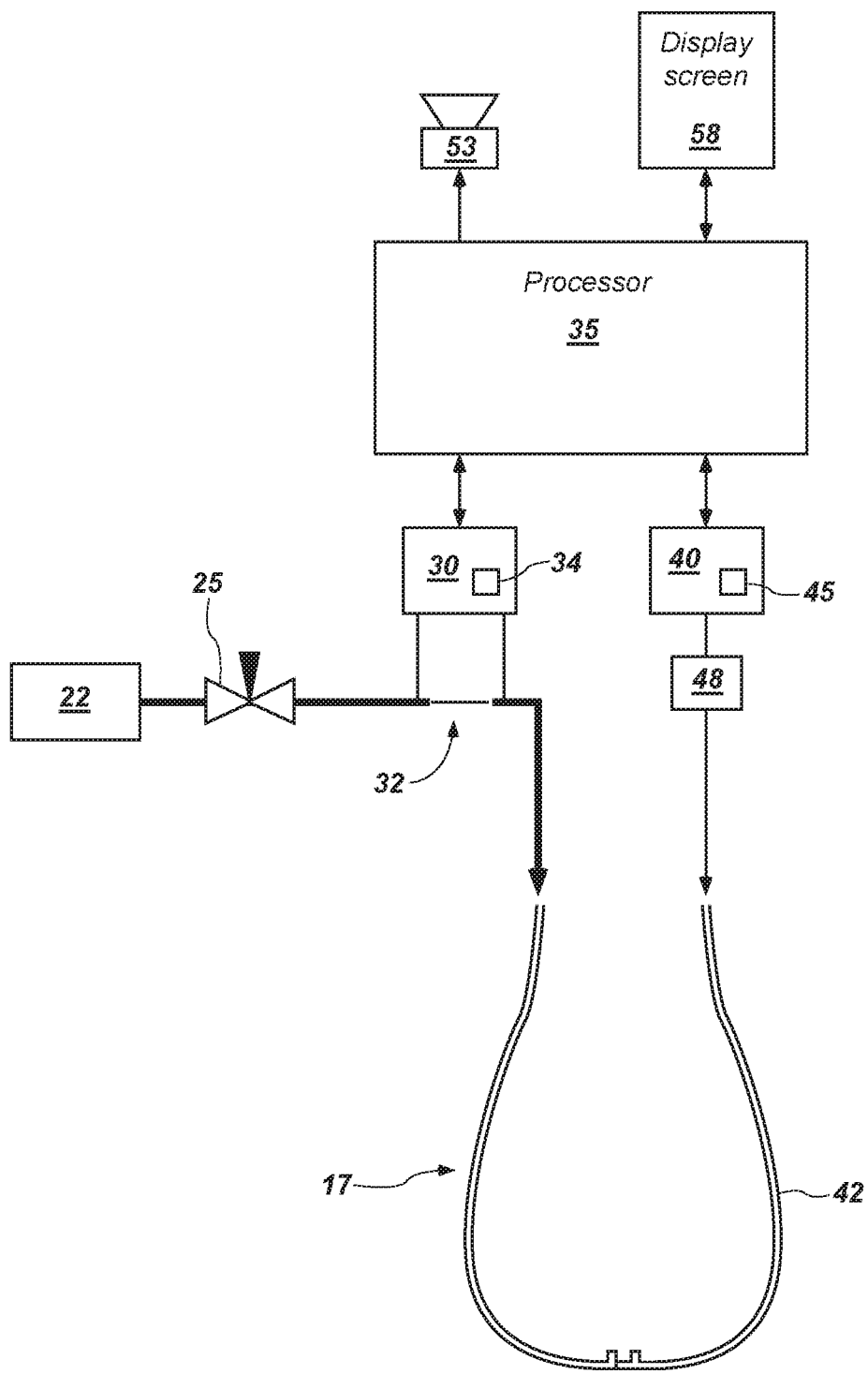
FIG. 1 is a diagram of a system in clinical practice that can determine the source of oxygen delivery failure to a patient and/or calculate the fraction of delivered oxygen that is inhaled by a patient.

A perspective view of the apparatus for identifying the source of oxygen delivery failure to a patient, as it may be used in clinical practice, is shown in FIG. 1. In clinical practice, the patient is provided with an oxygen delivery device 17. The oxygen delivery device 17 may be a nasal cannula, as shown in FIG. 1, such as a single- or double-nared nasal cannula, or it may be a mask or other device. The oxygen delivery device 17 is provided with a connection, such as tubing, to an oxygen source 22. It may be desirable to provide a flow control valve 25 in connection with the oxygen source 22 so the medical personnel can select, adjust, or control the oxygen flow rate from the oxygen source 22.

The flow control valve 25 may be a simple needle valve. The flow control valve may be a simple ON/OFF type valve that has only two positions: open and closed. In one configuration, the flow control valve 25 may provide a variable flow. The flow control valve 25 may be connected to the processor 35 and may deliver a variable gas flow. For example the processor may set a flow rate that changes up to 100 times per second according to variables such as the desired oxygen delivery for the particular patient and the measure oxygen delivery to the patient. The variable-type of flow control valve 25 may be, for example, those known in the art such as the EVP Series Proportional Control Valves manufactured by Clippard Instrument Laboratory, Inc.

Additionally, at some point in the tubing between the patient 14 and the oxygen source 22, an oxygen flow analyzer 30 may be provided. The oxygen flow analyzer 30 measures an oxygen flow rate to provide an oxygen flow rate value. The oxygen flow analyzer 30 may be of any type known in the art, and in one configuration may be a simple differential pressure system. For example, a slight obstruction, such as a section of tubing having a smaller inner diameter 32, is placed in the oxygen flow tubing within the system, and a differential pressure analyzer measures the pressure difference caused by the flow interruption. The measured differential pressure is then used to calculate the corresponding oxygen flow rate. Another type of suitable oxygen flow analyzer 30 could be a heated wire-type anemometer. It may be desirable to include a barometer in the system and compensate for the change in gas density and various altitudes.

The oxygen flow analyzer 30 may be equipped with its own oxygen flow analyzer processor 34 to calculate the oxygen flow rate value from the measured parameters. The oxygen flow analyzer processor 34 may then communicate the oxygen flow rate value to a processor 35. Alternatively, the oxygen flow analyzer 30 may be in communication with a processor 35 to provide the processor 35 with the measured parameters necessary for the processor 35 to calculate the oxygen flow rate value. The processor 35 may be programmed to store and analyze the oxygen flow rate values received from the oxygen flow analyzer processor 34 or the oxygen flow rate values calculated by the processor 35.

The apparatus for identifying the source of oxygen delivery failure to a patient may also include a pressure sensor 40. The pressure sensor 40 may be a precision, low-pressure sensor. The pressure sensor 40 is in communication with the patient such that the pressure sensor 40 detects a patient's breathing pressure. For example, if the patient is using a mask as an oxygen delivery device 17, the pressure sensor 40 may be in communication with the mask by tubing 42. In the case of a nasal cannula as the oxygen delivery device 17, a piece of tubing 42 in communication with the pressure sensor may be placed in one (or both) of the patient's nostrils. In one configuration, the pressure sensor is provided with a port that allows simple insertion of a piece of tubing 42. The tubing 42 can then be placed either on the patient's mask or in a patient's nostril(s). Additionally, the pressure sensor 40 may be disposed anywhere along the tubing it is desired. For example, the pressure sensor 40 may be placed very close to a patient's oxygen delivery device 17, or the pressure sensor 40 may be placed farther from the patient and closer to the medical personnel and other medical instruments.

The pressure sensor 40 detects a patient's breathing pressure, including the inhalations, which are detected as a negative pressure, and the exhalations, which are detected as a positive pressure. The plurality of breathing pressure values measured by the pressure sensor 40 may be analyzed by a pressure sensor processor 45 and communicated to the processor 35. Alternatively, the plurality of breathing pressure values measured by the pressure sensor 40 may be communicated to the processor 35 and the processor 35 may analyze the breathing pressure values.

The apparatus for identifying the source of oxygen delivery failure to a patient may also be provided with a device to measure the ambient pressure. In one configuration, this may be a separate pressure sensor to measure ambient pressure. In another configuration, the pressure sensor 40 is in communication with a solenoid valve 48. Either the processor 35 or a pressure sensor processor 45 may direct the opening and closing of the solenoid valve 48. Typically, the solenoid valve 48 will remain closed such that the pressure sensor 40 is measuring the patient's breathing pressure. Periodically, the solenoid valve 48 may be opened, and the pressure sensor 40 would then measure the ambient pressure. (The solenoid valve 48 could also be configured such that the open position measures the patient breathing pressure and the closed position measures the ambient pressure.) The ambient pressure measurement may be used to determine an ambient pressure value. Again, this may be achieved through the use of a separate processor, such as the pressure sensor processor 45, with the pressure sensor processor 45 communicating the ambient pressure value to the processor 35; alternatively, the ambient pressure measurement may be communicated to the processor 35, and the processor 35 may determine the ambient pressure value.

The processor 35 may receive data from the oxygen flow analyzer 30 (or from the oxygen flow analyzer processor 34) and the pressure sensor 40 (or the pressure sensor processor 45). The processor may be provided with one or more input ports to receive data, and one or more output ports. The processor may be programmed to output an apnea alarm, an insufficient oxygen flow alarm, or an oxygen delivery device displacement alarm. These alarms may be, for example, audible alarms, visual alarms, or both. The processor 35 may output, for example, to a speaker 53 and/or a visual indicator. In one configuration, the processor is in communication with a display screen 58 that allows a user to select parameters for the processor. The processor may also output alarms and data to the display screen.

The processor 35 analyzes that data it receives to determine the source of oxygen failure to a patient. The logic of the processor comprises two general steps: (1) analyzing the plurality of breathing pressure values to determine if a patient is breathing, and (2) comparing the plurality of breathing pressure values to the ambient pressure value when the processor determines the patient is not breathing and the oxygen flow rate value is greater than a predetermined threshold.

Figure 2:
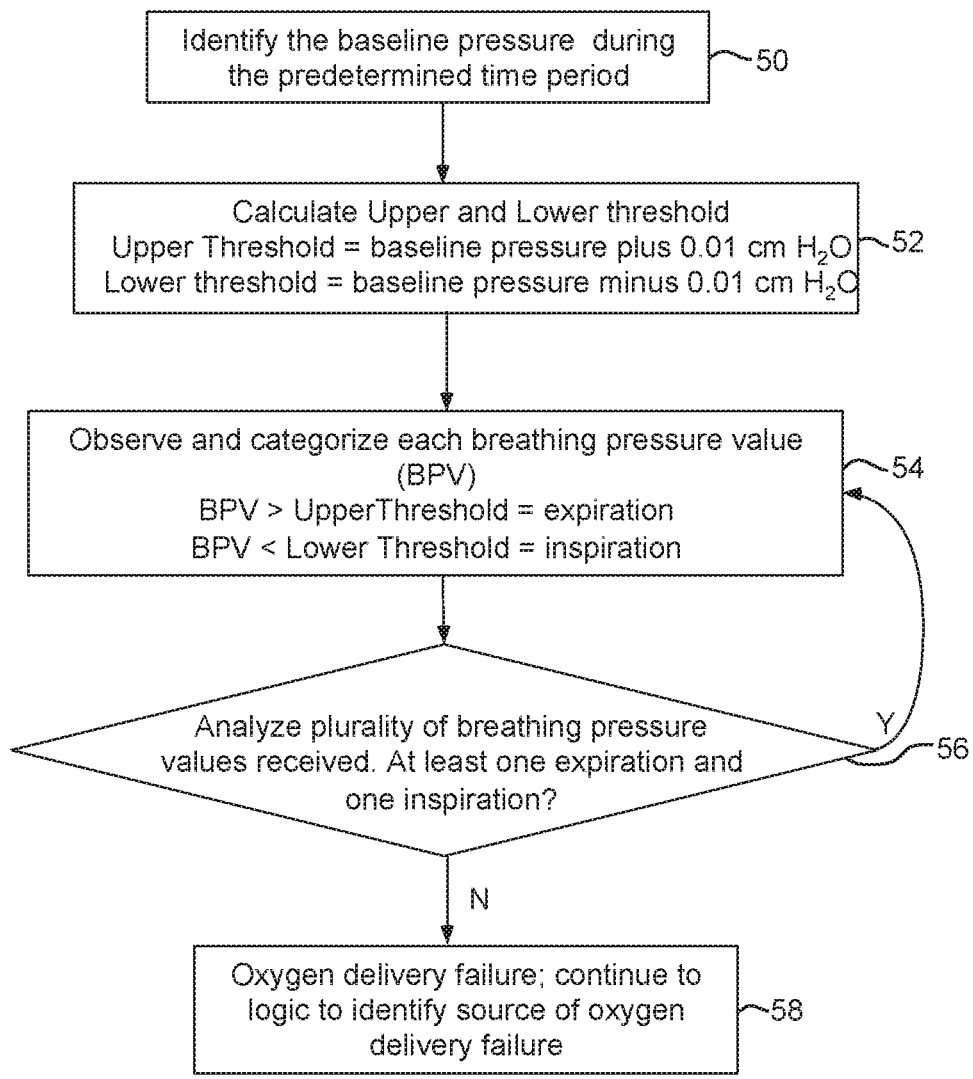
FIG. 2 is a flow chart illustrating the logic to determine whether a patient is breathing or not.

In the first step, the logic of the processor 35 analyzing the plurality of breathing pressure values to determine if a patient is breathing, the logic comprise any suitable logic, such as those already known in the art. FIG. 2 is a flow chart that describes an operable method to analyze the plurality of breathing pressure values to determine if a patient is breathing. The processor may first calculate a baseline pressure 50. The baseline pressure may be calculated by measuring the pressure at the time between a patient's breaths, i.e., the pause between inspiration and expiration. At that time, the only measured pressure should ideally be a slight positive pressure due to the flow of oxygen. Other suitable methods to calculate the baseline pressure include calculating the average of the pressure values during a predetermined time period, calculating the median pressure value during a predetermined time period, etc.

Once the processor determines a baseline pressure, the processor may calculate an upper threshold value and lower threshold value by adding and subtracting, respectively, a small offset, such as 0.01 cm $H_2O$, shown in FIG. 2 at 52. The processor then observes each breathing pressure value and categorizes it as an expiration, inspiration, or insignificant (54). For example the processor may receive one breathing pressure value every 10 milliseconds (100 breathing pressure values per second). Each breathing pressure value may be analyzed and categorized. To determine if a patient is breathing, the processor checks for both an inspiration and an expiration during a pre-determined time period (56). This pre-determined time period may be, for example, 10 seconds. In one configuration, the processor may have an interface, such as a display screen, to allow medical personnel to select the pre-determined time period they desire for a particular patient. As shown in FIG. 2, if both an inspiration and an expiration are detected during the pre-determined time period, the patient is breathing, and the processor continues to analyze breathing pressure values over the next pre-determined time period. If both an inspiration and an expiration are not detected during the pre-determined time range, then the patient is not breathing, and the processor continues to the logic to identify the source of oxygen delivery failure to the patient (58).

Figure 3:
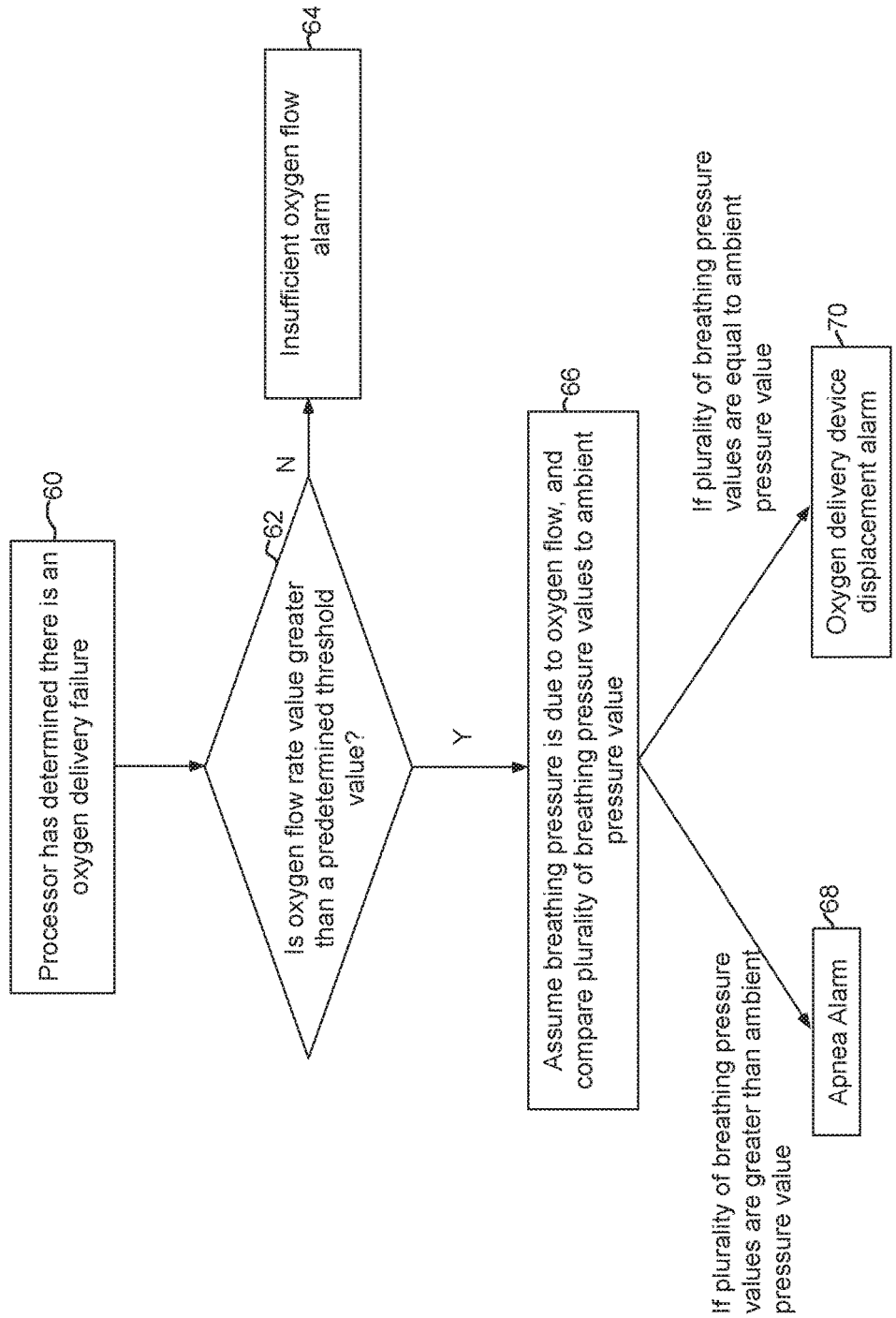
FIG. 3 is a flow chart illustrating the logic to determine the source of oxygen delivery failure to a patient.
Figure 4:
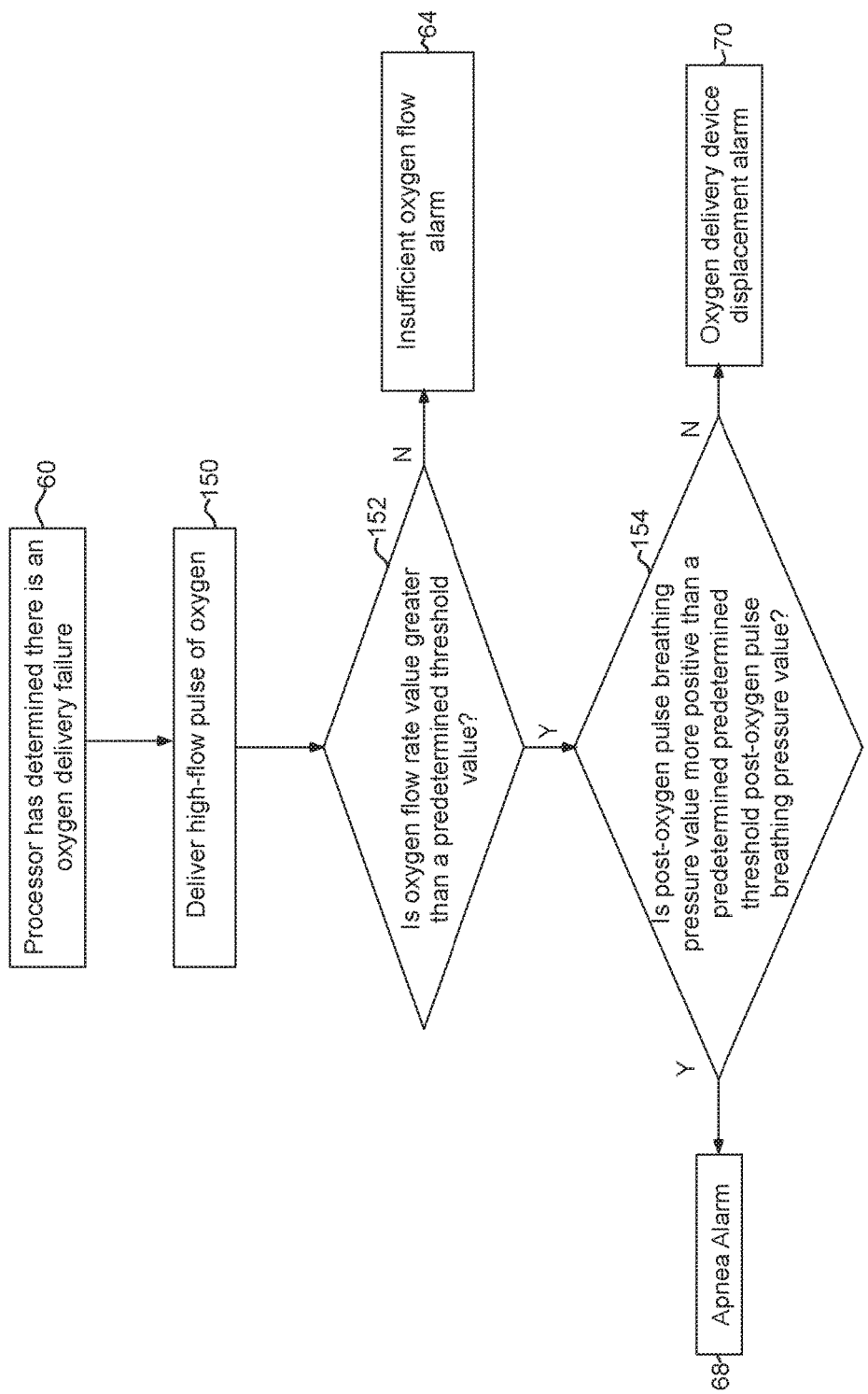
FIG. 4 is a flow chart illustrating another logic that may be used to determine the source of oxygen delivery failure to a patient.

The logic for identifying the source of oxygen delivery failure to a patient may include the steps shown in FIG. 3. While the logic shown in FIGS. 2-4 shows discrete steps taken in order, the steps need not be taken in the particular order shown. For example, the processor may be programmed to continuously check the oxygen flow rate value and trigger an oxygen flow rate alarm at any time the oxygen flow rate value is less than a predetermined threshold. Similarly, the processor may be programmed to periodically (or continuously) sample the ambient pressure. The steps may be taken in a different order and still achieve the desired outcome. In FIG. 3, after the processor logic has determined the patient is not breathing (60), the processor may determine if there is sufficient oxygen flow. This may be done, for example, by the processor analyzing the oxygen flow rate value to determine if it is greater than a predetermined threshold value (62). In one configuration, this predetermined threshold value may be 0.5 liters per minute. In another configuration, the processor 35 may include an interface which allows medical personnel to select the desired predetermined threshold value for oxygen flow rate. If the processor determines that the oxygen flow rate value is less the predetermined threshold value, the processor may trigger an insufficient oxygen flow alarm (64). This alarm may be an audible alarm, a visual alarm, or it may be both audible and visual. If the processor determines that the oxygen flow rate value is greater than the predetermined threshold value, the processor further compares the plurality of breathing pressure values to the ambient pressure value (66). The processor may compare the plurality of breathing pressure values to a stored ambient pressure value, or the processor may be programmed to sample the ambient pressure value when it is determined that a patient is not breathing and the oxygen flow rate value is greater than the predetermined threshold value. When the processor determines the plurality of breathing pressure values are greater than the ambient pressure value, the processor outputs an apnea alarm (68). When the processor determines the plurality of breathing pressure values are equal to the ambient pressure value, the processor outputs an oxygen delivery device displacement alarm (70).

The apnea alarm and the oxygen delivery device displacement alarm may be audible alarms, visual alarms, or both. In one configuration, the apnea alarm may be louder and/or have greater visibility than the oxygen delivery device displacement alarm. This configuration may be preferred since apnea is an immediate life-threatening danger and requires medical personnel to respond immediately, whereas oxygen delivery device displacement may be less hazardous.

In another configuration, the processor may determine whether there is insufficient oxygen flow by measuring the oxygen flow rate in response to a known voltage on the flow control valve 25 to determine if there is an insufficient oxygen flow. This configuration is shown in FIG. 4. The processor may first determine that there is an oxygen delivery failure (60). This may be done by performing the steps indicated in FIG. 2, or the processor may be programmed to routinely check for oxygen delivery failure. When the processor determines there is an oxygen delivery failure (60), the processor 35 sends a signal to the flow control valve 25 to increase the voltage on the flow control valve to a known, high voltage to deliver a high-flow pulse of oxygen (for example, 5-15 Liters/min for 50-200 milliseconds)(150). The system then measures the oxygen flow rate value in response to the high-flow pulse of oxygen (152). When oxygen flow is sufficient and there are no issues with the oxygen delivery, the increased voltage on the flow control valve 25 should result in an increase in the measured oxygen flow by the oxygen flow analyzer 30. The system may be programmed to have a predetermined threshold valve for the oxygen flow rate value in response to the voltage (for example, an oxygen flow rate value of 5 L/min). If the oxygen flow analyzer 30 measures an oxygen flow rate value above the predetermined threshold value, due to the increase in voltage on the flow control valve, there is not an issue with oxygen delivery. If the processor sends a signal to the flow control valve 25 to increase the voltage and the oxygen flow analyzer 30 does not measure an oxygen flow rate value above the predetermined threshold value, there is a problem with oxygen delivery and the system may trigger an insufficient oxygen flow alarm (64).

If there is sufficient oxygen flow in response to the high-flow pulse of oxygen, the processor may then analyze the breathing pressure value, post-oxygen pulse (taken by pressure sensor 40) to determine if the post-oxygen pulse breathing pressure value is greater than a predetermined threshold value (154). If the oxygen delivery device 17 is in place, the high-flow pulse of oxygen should cause an increased positive pressure at the oxygen delivery device 17. A pre-determined threshold value for the post-oxygen pulse breathing pressure value in response to the high-flow pulse of oxygen may be programmed into the processor 35, and the post-oxygen pulse breathing pressure value may be compared to the pre-determined threshold value. If the post-oxygen pulse breathing pressure value is less negative, it is an indication that the oxygen is being lost into the ambient pressure of the room, and an oxygen delivery device displacement alarm may be triggered (70). If the post-oxygen pulse breathing pressure value is more negative, it is an indication that the patient is receiving the high-flow pulse of oxygen and not breathing, and an apnea alarm (68) may be triggered.

Figure 5:
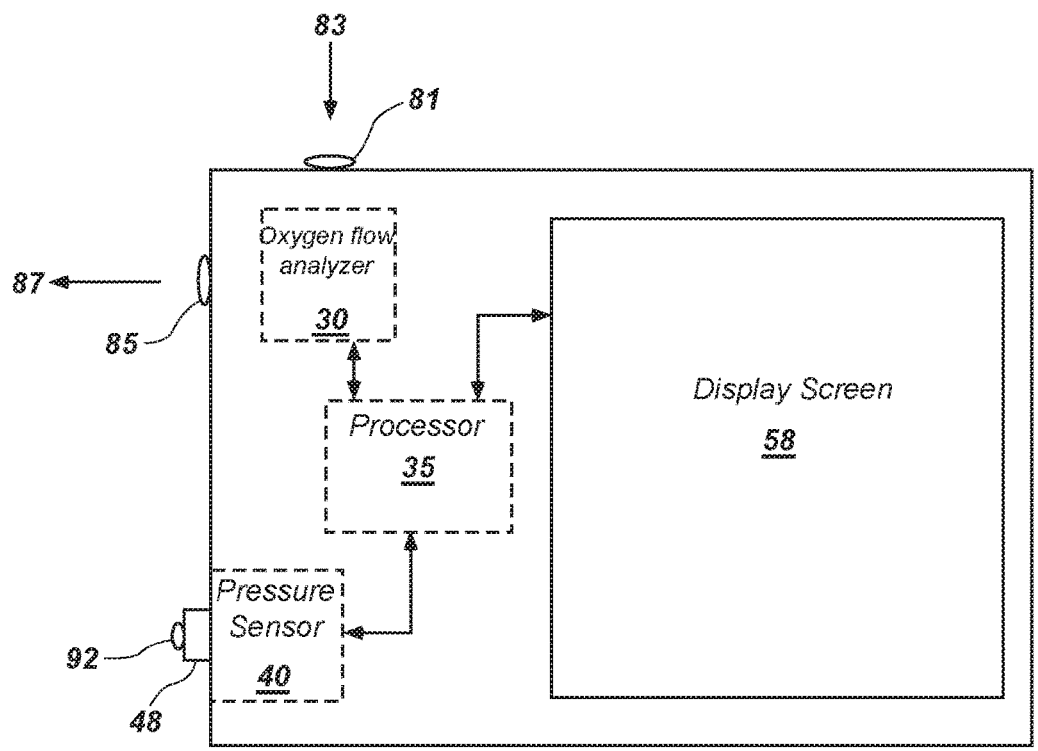
FIG. 5 is a diagram of an apparatus to determine the source of oxygen delivery failure to a patient and/or calculate the fraction of delivered oxygen that is inhaled by a patient.

In one configuration, the processor, oxygen flow analyzer, and pressure sensor are contained in a single housing, such as that shown in FIG. 5. The housing 80 comprises an input port 81 for receiving tubing (not shown) from an oxygen source, and an output port 85 for the oxygen that flows into the housing and through the oxygen flow analyzer 30 to flow to the oxygen delivery device of the patient. The oxygen may flow into the housing from an oxygen source in the direction of the arrow 83 and out of the housing to the patient delivery device in the direction of the arrow 87. The housing also comprises a port 92 for a tube to be connected from the oxygen delivery device of the patient to the pressure sensor 40 located in the housing. This may also be in communication with a solenoid valve 48, such that the pressure sensor 40 may detect the pressure of the patient breathing or the ambient pressure.

The housing may include an interface, such as a screen 58, for medical personnel to set specific parameters of operation, such as what time increments the breathing pressure sensor will sample for breathing pressure values, what time increments the solenoid valve will open or close to sample the ambient pressure, the predetermined threshold value for oxygen flow, and/or the predetermined time period for one inhalation and one exhalation to be detected in order to determine the patient is breathing. In some configurations, the medical personnel can select to have these parameters set as defaults that will work for a majority of patients. In another configuration, one or more of these parameters may be specifically selected by medical personnel for the needs of a particular patient.

According to another aspect, the method may include the processor calculating a volume of oxygen inhaled by a patient during a predetermined time period. The processor 35 may be programmed to calculate the volume of inhaled oxygen using the formula $$\text{flow} = K\sqrt{\text{pressure}}$$

In this formula, there is a square law relationship between flow and pressure. The factor K accounts for the gas flow resistance created by the particular patient's nostril and the placement of the cannula within the nostril (or, in the case of a mask, the placement of the mask on the patient). It is known that for any orifice defining a pressure drop between a pressurized system and a lower pressure surrounding environment (i.e., ambient pressure), the flow through the orifice will be proportional to the square root of the pressure difference across the orifice multiplied by a constant K which characterizes the mechanical features of the orifice itself, that is its size, surface smoothness, and so forth. K is not a constant and is normally not known because it varies from patient to patient, but may be calculated with the current system. Flow is the calculated flow rate of the oxygen flowing past the oxygen delivery device (either a mask or a cannula). Pressure is the pressure difference between the ambient pressure measured by opening solenoid valve 48 on pressure sensor 40, and the breathing pressure at the oxygen delivery device 17 measured by pressure sensor 40 (breathing pressure at the oxygen delivery device 17 is caused by both the patient's breathing pressure and the oxygen flow pressure).

Within the system, the oxygen flow is being determined by the oxygen flow analyzer 30, and the pressure sensor 40 allows the determination of the baseline pressure caused by the oxygen flow (as described above). When a patient is not breathing and there is no oxygen flow, the oxygen flow and the baseline pressure should both be zero. Typically, a patient has a pause at the end of expiration before the next inhalation begins. At this pause, the only source of pressure detected by the pressure sensor 40 is from the oxygen flow (rather than pressure detected from oxygen flow plus a patient's breathing). And the oxygen flow that is inducing the non-zero pressure is known since the oxygen flow is directly measured in the system by the oxygen flow analyzer 30. Thus, K may be calculated at the pause, where flow and pressure are known, using $$K = \frac{\text{flow}}{\sqrt{\text{pressure}}}$$

Flow here is the oxygen flow value determined by the oxygen flow analyzer 30, and the pressure is the breathing pressure value determined by the pressure sensor 40. The factor K can then be stored in the processor 35. The stored K-factor can be used in the equation flow=K√pressure to determine the patient's breathing flow value from the pressure signal for every pressure signal sampled.

Figure 6:
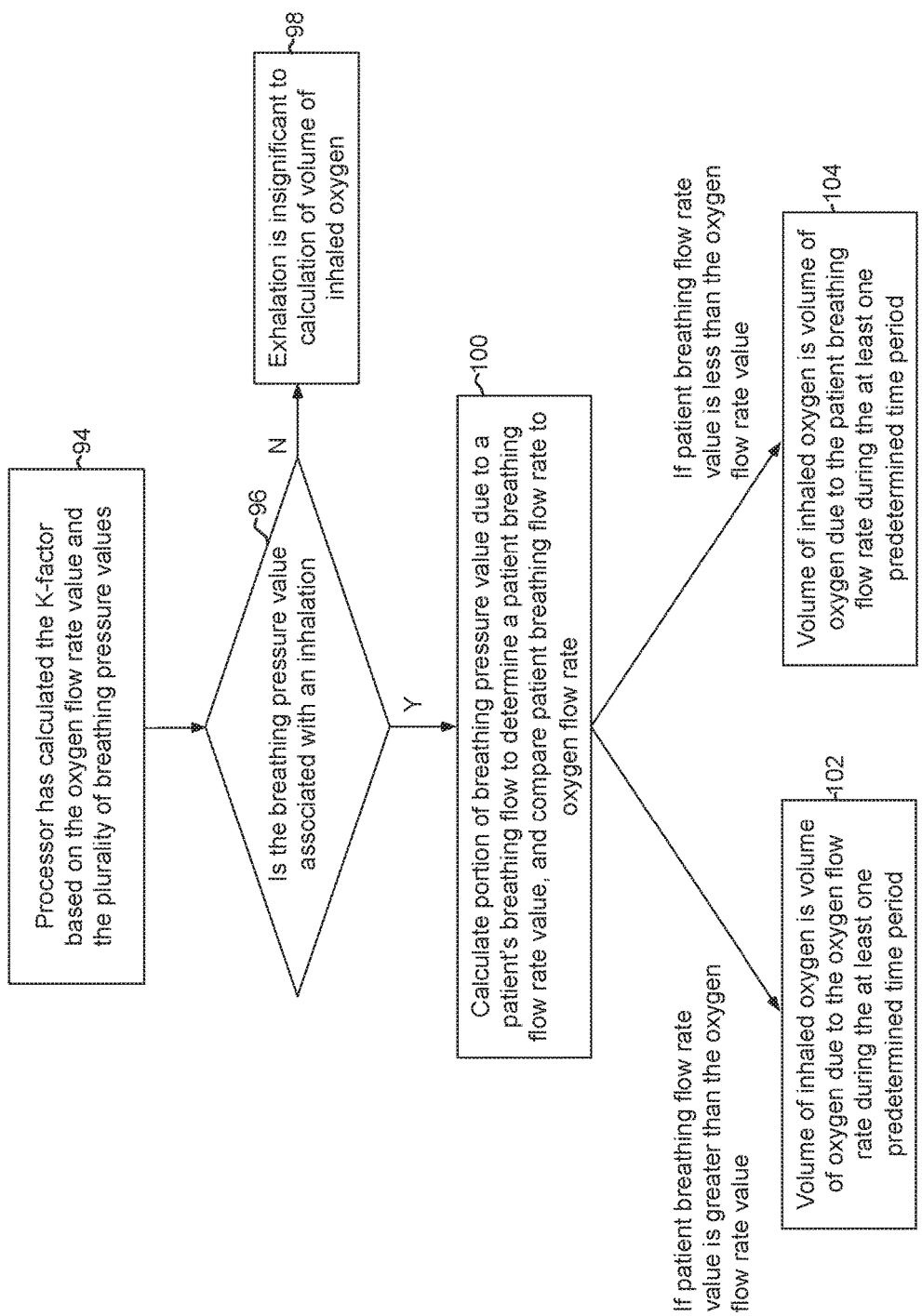
FIG. 6 is a flow chart illustrating the logic to calculate a volume of delivered oxygen that is inhaled by a patient.

The system also may assume that no delivered oxygen is being inhaled while a patient is exhaling. Likewise, the system may assume that all delivered oxygen is being inhaled when a patient is inhaling at a patient breathing flow greater than the delivered oxygen flow. As shown in the logic of FIG. 6, the processor may first calculate the K-factor, as described above (94). The processor may analyze breathing pressure values received to classify each as an inhalation or expiration (96). Based on the assumption that no delivered oxygen is being inhaled while a patient is exhaling, expirations are insignificant in the calculation of inhaled oxygen (98). For each breathing pressure value classified as an inhalation, the system may use the equation above to calculate a portion of the breathing pressure value due to a patient's breathing flow to determine a patient breathing flow rate value (100).

The processor may then compare the patient breathing flow rate value to the oxygen flow rate value (100). When the patient breathing flow rate value is greater than the oxygen flow rate value, the processor may calculate the volume of inhaled oxygen as the volume of oxygen due to the oxygen flow rate during the predetermined time period (102). When the patient's breathing flow rate value is less than the oxygen flow rate value, the processor may calculate the volume of inhaled oxygen as the volume of oxygen due to the patient breathing flow rate during the time period (104). For each breathing pressure value classified as an inhalation, the processor may perform the steps above to determine the volume of inhaled oxygen during the time period. The processor may be programmed to further add the volume of inhaled oxygen during multiple time periods together to determine a volume of inhaled oxygen over a longer time period. Moreover, the steps to calculate the volume of inhaled oxygen need not be performed in the particular order shown in FIG. 6. For example, the processor 35 may first classify a breathing pressure value as an inhalation or exhalation, and then determine the K-factor. Likewise, these steps may be performed simultaneously by the processor 35.

Figure 7:
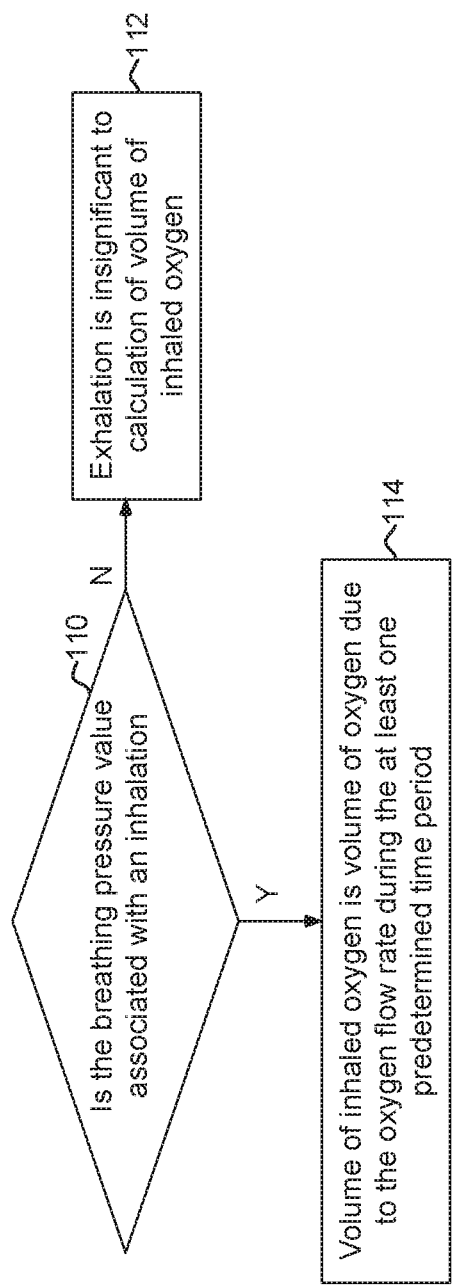
FIG. 7 is a flow chart illustrating another logic that may be used to calculate a volume of delivered oxygen that is inhaled by a patient.

Turning now to FIG. 7, there is shown another example of logic that may be used to calculate the volume of inhaled oxygen. It should be appreciated that while the steps in FIG. 7 are shown in a particular order, the steps may be performed in a different order. Similarly, while the steps are shown separately, one or more steps may be performed at the same time. According to this logic, the processor 35 analyzes the breathing pressure value from the pressure sensor 40 to determine if the breathing pressure value is associated with an inhalation (110). This may be done, for example, by comparing the breathing pressure value with a pre-determined threshold value. If the breathing pressure value is lower (or more negative), the patient is inhaling. The processor may also be programmed to associate any negative breathing pressure value as an inhalation.

If the breathing pressure value is not associated with an inhalation, the patient is determined to be exhaling, and exhalation is insignificant to the calculation of the volume of inhaled oxygen (112). If the breathing pressure value is associated with an inhalation, the processor 35 may be programmed to assume that the volume of inhaled oxygen during the predetermined time period is due to the oxygen flow rate (i.e., the oxygen flow rate for the predetermined time period, as measured by the oxygen flow analyzer 30, multiplied by the predetermined time period)(114).

Figure 8:
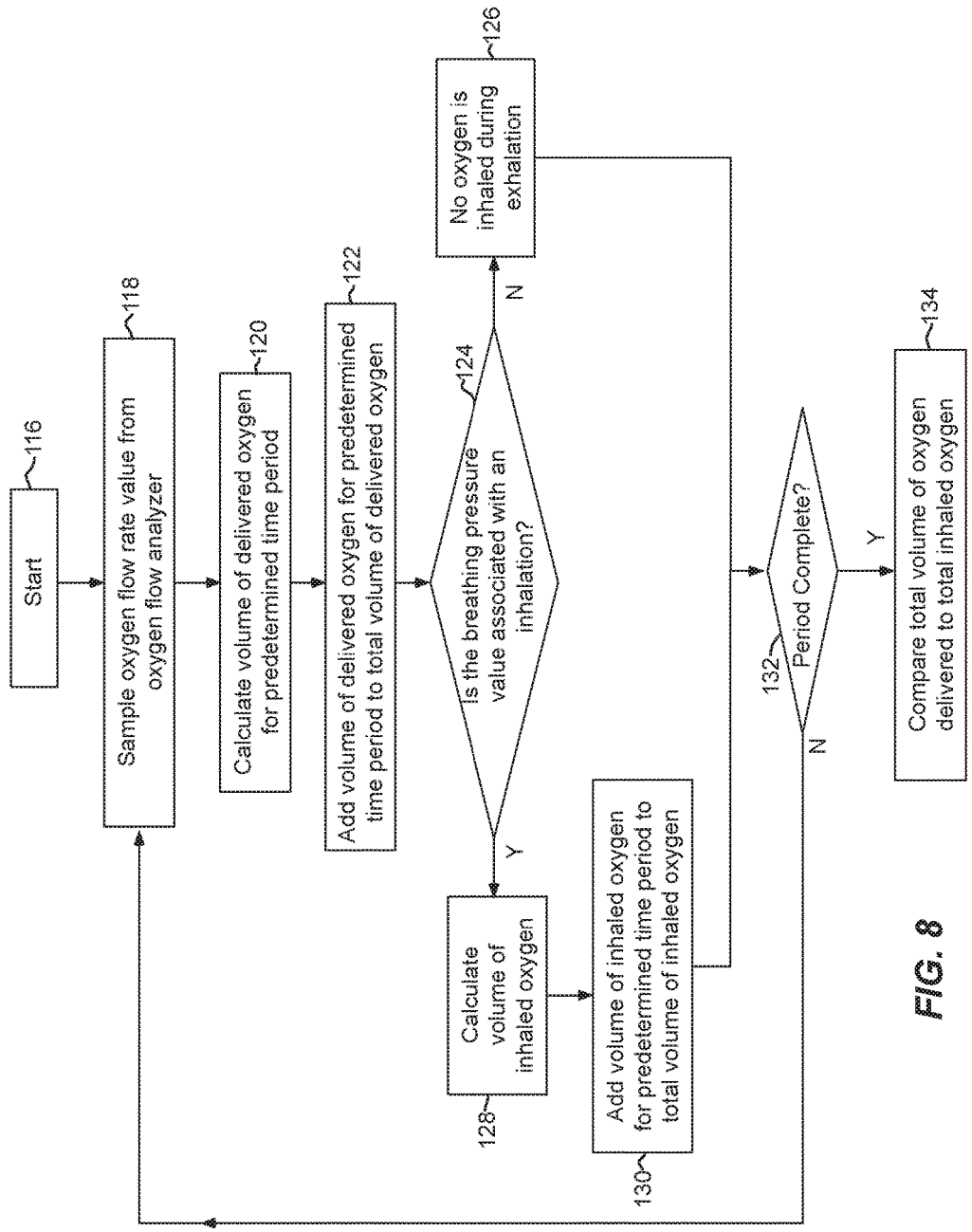
FIG. 8 is a flow chart illustrating the logic to calculate the total volume of oxygen to be delivered to a patient.

FIG. 8 shows the logic the processor 35 may follow to calculate a total volume of inhaled oxygen over a greater time period (for example, 1 minute) by calculating the volume of oxygen inhaled during each predetermined time period (for example, 1 millisecond) within the greater time period, and adding them together. The processor starts (116) and samples the oxygen flow rate value from the oxygen flow rate analyzer 30 (118). The processor then uses this oxygen flow rate value to calculate the volume of oxygen delivered for the predetermined time period (120), by multiplying the oxygen flow rate value by the predetermined time period (for example, an oxygen flow rate value of 6 L/min times a predetermined time period of 10 milliseconds, for a volume of 1 mL of oxygen delivered).

The processor then adds the volume of oxygen delivered for the predetermined time period to the total volume of oxygen delivered (122). The total volume of oxygen delivered is incremented each predetermined time period by the volume of oxygen delivered during that predetermined time period. The processor then analyzes the breathing pressure value from the pressure sensor 40 to determine if the breathing pressure value is associated with an inhalation (124), which may be done by the methods described above (i.e., determining if the breathing pressure value is below a threshold value or if the breathing pressure value is negative, etc.).

If the breathing pressure value is not associated with an inhalation, no oxygen is delivered during exhalation (126), and the processor will determine if the period is complete (132). If the period is not complete, the algorithm continues by sampling the oxygen flow rate value for the next predetermined time period (118) and continuing through the loop. If the breathing pressure value is associated with an inhalation, the processor calculates the volume of inhaled oxygen during the predetermined time period (128). This may be done, for example, using the steps outlined in FIG. 6 or FIG. 7 (using the predetermined flow rate, either from the oxygen flow rate or the patient breathing flow rate, multiplied by the predetermined time period). The processor then adds the volume of inhaled oxygen for the predetermined time period to the total volume of inhaled oxygen (130). The processor then determines if the period is complete (132) (i.e., if the time period, such as one minute, is over). If not, the algorithm continues by sampling the oxygen flow rate value for the next predetermined time period (118) and continues the loop until the period is over.

When the period is complete, the processor may be programmed to then compare the total volume of inhaled oxygen to the total volume of delivered oxygen (134). The processor may output a percentage of inhaled oxygen. This output may be displayed to clinicians on a display screen (FIG. 5). The clinician may be able to select what parameters of data to display, for example, what fraction of oxygen is inhaled, what fraction of oxygen is wasted, etc.

According to another aspect, the system described herein may be used to control oxygen delivery in a specific manner. By using the pressure sensor 40 to determine when, and at what rate, the patient is inhaling, the system may deliver a targeted amount of oxygen to the patient. Moreover, the flow control valve 25 may adjust the oxygen flow rapidly in response to the patient's sensed breathing pressure, and provide a variable oxygen flow rather than merely an "on/off" control. This may have the advantage of reducing wasted delivered oxygen (when the delivered oxygen is not inhaled but rather lost to the ambient air) and also increasing the amount of oxygen actually delivered to the patient. This may also reduce the flammability risk that is inherent in the use of oxygen delivery.

The flow control valve 25 may be any suitable valve known in the art, such as the EPV proportional control valves manufactured by Clippard mentioned above. These valves have a solenoid, and are capable of varying oxygen flow based on the current input to the solenoid. Greater current input to the solenoid opens the valve further, and a precise degree of control over the flow rate is possible. A single flow control valve 25 may be used, or more than one flow control valve can be used in conjunction.

In one configuration, the processor may first optimize the oxygen flow for the particular patient such that pressure at the oxygen delivery device equals the ambient pressure in the room. (Except possibly in cases of deep inhalations, where it is clinically impractical to deliver such a high oxygen flow, and usually not necessary for a patient who is taking deep inhalations.)

The ambient pressure in the room may be measured by the opening the solenoid valve 48 on the pressure sensor 40. Alternatively, the ambient pressure may be measured by an ambient pressure sensor 44 in communication with the processor 35. The ambient pressure value is sent to the processor 35. The processor uses the ambient pressure value to determine an optimal oxygen flow value (which is equal to the ambient pressure value). The processor then sends a signal to the flow control valve 25 to increase or decrease the oxygen flow, and this process is continued until the oxygen flow is optimized for the particular patient, that is, until the pressure at the oxygen delivery device 17 equals the ambient pressure. If the pressure at the oxygen delivery device 17 is any greater, i.e., the pressure is positive, and oxygen is lost into the room. If the pressure is lower, a critical opportunity to deliver oxygen to the patient is lost. It may not be possible to deliver a flow of oxygen sufficiently high at the start of the breath if the patient is taking deep breaths, but the processor may send a signal at that point to deliver the maximum flow rate possible.

The processor continues to send the signal to the flow control valve 25 to maintain the flow of oxygen (such that the pressure at the oxygen delivery device 17 equals the ambient pressure) until the predetermined amount of oxygen has been inhaled for that breath, or until the pressure sensor 40 indicates the patient has started to exhale. No oxygen is delivered during exhalation. Patients in opioid induced respiratory depression have short periods of inspiration relative to long pause periods between breaths. By delivering the highest flow of oxygen at the start of inspiration, oxygen flow is optimized so that it is most likely to be drawn deep into the lungs.

According to another aspect, the amount of oxygen delivered to the patient may be based on a calculation of the oxygen they have already inhaled and the amount of oxygen the patient still needs to inhale based on parameters set by the clinician. In this configuration, the clinician may determine a set amount of oxygen flow that they desire the patient to receive, based on the particular patient's current condition. This is the "pre-selected oxygen flow rate," and may be optimized for each patient. For example, it may be desired that the patient receive a flow of oxygen of 6 liters per minute (6 L/min). However, merely setting a traditional oxygen delivery device to 6 L/min does not ensure that the patient receives all the oxygen that should be delivered at this rate. According to the principles taught herein, the flow control valve can deliver precise amounts of oxygen in a given time interval to ensure the patient receives the desired amount of oxygen. The pre-determined time interval may be set by the clinician via the processor 35. By way of example, the pre-determined time interval may be 10 milliseconds.

Figure 9:
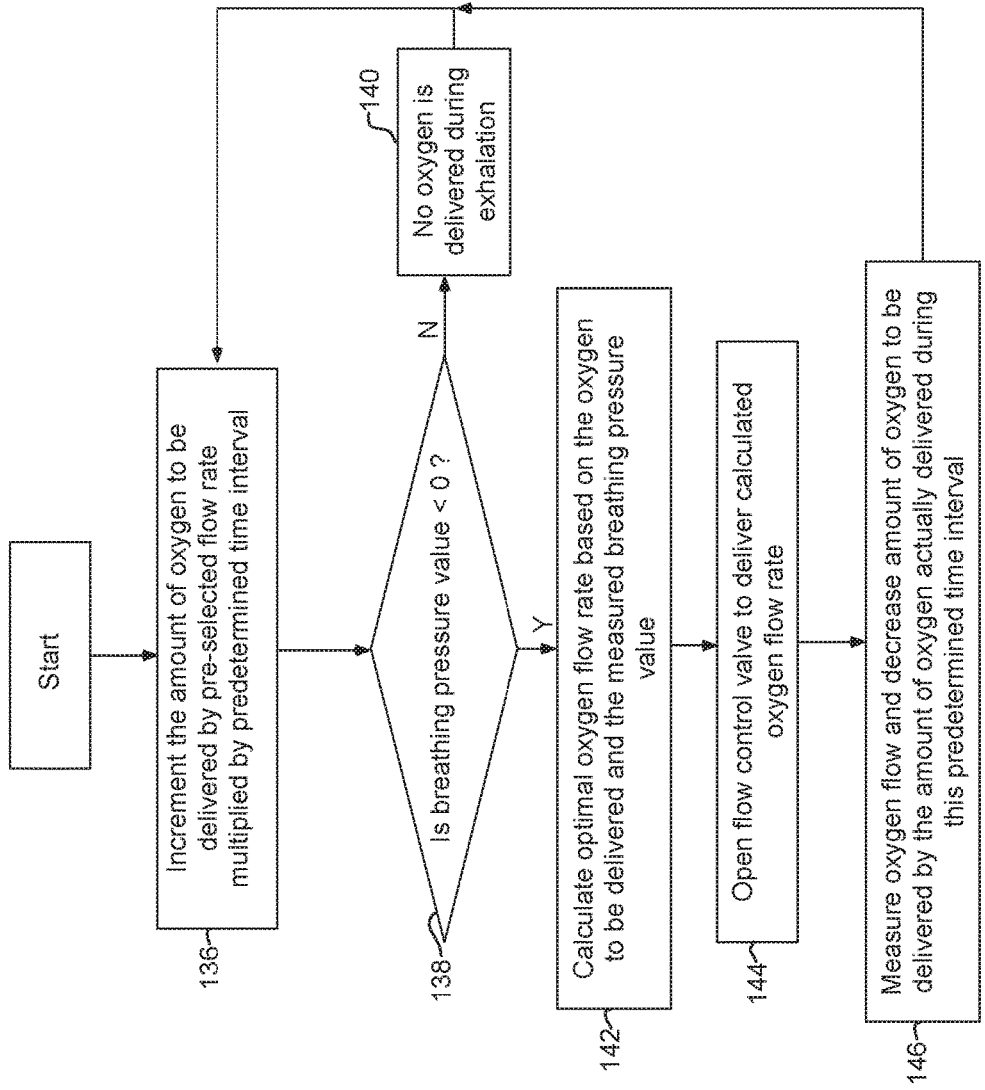
FIG. 9 is a flow chart illustrating the logic to deliver a variable flow of oxygen to a patient based on the total volume of oxygen to be delivered to the patient.

The processor 35 may perform an algorithm for every pre-determined time interval (for example, every 10 milliseconds) to determine the precise flow to deliver for that time interval. The algorithm may include the steps shown in FIG. 9. It should be appreciated that while the steps in FIG. 9 are shown in a particular order, the steps may be performed in a different order. Similarly, while the steps are shown separately, one or more steps may be performed at the same time.

In one configuration, the processor 35 may automatically adjust to account for that fact that a typical patient is only inhaling during one third of the time. So if the clinician selected a flow rate of 6 L/min, the processor 35 may assume that the patient only inhales one-third of the time, and will set a rate of oxygen delivery of 2 L/min. In other configurations, the processor may be set to calculate the oxygen increment with or without this assumption.

The amount of oxygen the processor 35 calculates to be delivered in any given time interval is the amount of oxygen in the oxygen backlog. The oxygen backlog is the amount of oxygen that is to be delivered, but has not yet been delivered. For each predetermined time interval, the oxygen backlog is incremented or increased by at least the oxygen to be delivered based on the clinician's pre-selected oxygen flow rate (136 in FIG. 9). Oxygen to be delivered based on the pre-selected flow rate is calculated as follows: the set flow rate (i.e. 2 L/min) multiplied by the predetermined time interval (i.e. 10 mSec, or 6000 per minute). For example, where the pre-selected oxygen flow rate is 2 L/min, or 2000 mL/minute, and the predetermined time interval is 10 mSec, it would be 2000 mL/min multiplied by 10 mSec (or 2000 mL/min divided by 6000 predetermined time intervals per minute), resulting in a delivery of 0.333 mL per predetermined time interval. This is the amount of oxygen the processor 35 would calculate to deliver per time interval based on the pre-selected flow rate. Each time the processor 35 performs the algorithm shown in FIG. 9, or in other words, for each loop through the algorithm, the processor increments the oxygen backlog, or the oxygen to be delivered by this amount. Thus, for every predetermined time interval, the oxygen to be delivered is increased or incremented by this amount.

The processor 35 may also be programmed to track any backlog of oxygen that is not delivered during a predetermined time interval, and further increment the oxygen backlog for the next predetermined time interval by this amount. The processor may analyze the patient's breathing pressure value to determine if the breathing pressure value is negative or positive (138). (The processor may also determine if the patient is inhaling or exhaling by assuming that a breathing pressure value within the oxygen delivery device 17 above a pre-determined threshold value is an exhalation.) If the patient's breathing pressure is positive (exhale), the system is programmed to not deliver oxygen during an exhale (140), and the oxygen backlog for that predetermined time interval will not be delivered during that predetermined time interval. In the above example, for every predetermined time interval where the patient is exhaling, the oxygen backlog would be incremented by 0.333 mL. Or for each loop (from 136 to 138 to 140, and back to 136) through the algorithm during which the breathing pressure is positive, the oxygen backlog would be incremented by 0.333 mL.

In another example, if the clinician selected a flow rate of 2 L/min, the processor may automatically assume that only 666 mL would actually be inhaled, and adjust the set flow rate down accordingly. In this example with a flow rate of 2 L/min, the oxygen increment for each predetermined time interval (where a predetermined time interval is 10 mSec) would be 0.111 mL.

When the processor determines the patient is breathing, the processor may calculate an optimal oxygen flow rate based on the oxygen to be delivered (i.e., the oxygen backlog) and the measured breathing pressure value (142). The optimal oxygen flow rate is based on the following calculation:

$$\text{Optimal O2 flow rate} = \text{breathing pressure value} \times \text{factor} \times \text{oxygen backlog}$$

Where breathing pressure value is the breathing pressure value measured by the pressure sensor 40, the factor is a tuning constant based on the patient size, etc., and the oxygen backlog is the total amount of oxygen that needs to be delivered to the patient. As can be seen by this equation, the flow rate is based on the breathing pressure value, and will increase as the patient breathes deeper, and decrease as the patient's breath becomes more shallow (as at the end of a breath). Thus, in one breath, the optimal oxygen flow slows as the patient's own breathing slows. Similarly, the equation shows that the optimal oxygen flow is based on the oxygen backlog. As the backlog increases, the optimal oxygen flow rate will also increase.

The processor then opens the flow control valve to deliver the calculated optimal oxygen flow rate (144). This can be done by delivering a signal to the flow control valve using software (the software may be either integral to the valve, or integral to the processor 35) with a digital to analog converter that creates a voltage that is proportional to the digital value generated by optimal flow rate calculation. The voltage from the converter is fed into an analog circuit which generates a proportional electrical current that drives the valve. The volume of oxygen that flows through the valve during the sample period is directly proportional to the digital to analog convertor unit value. In one configuration, each converter unit corresponds to 0.005 mL of volume per sample period.

The breathing pressure value may be measured, for example, using a digital pressure sensor (for example, the DLVR models manufactured by All Sensors, Inc.), that converts the actual pressure in cm H2O into digital to analog converter units where 1 convertor unit is equal to 0.00031 cm H2O. To reduce the number of calculations, the algorithm may combine the unit conversion factors into the constant proportional control factor. This gives a control equation that is implemented in software as follows:

$$\text{Digital to analog convertor units output} = \text{AD convertor units} \times \text{oxygen backlog} \times K$$

Where digital to analog convertor units output is the digital to analog converter value that is used to generate the valve current and control the delivered oxygen rate; AD converter units is the digital output of the digital pressure sensor (where one unit equals 0.00031 cm H2O in the exemplary configuration above); Oxygen backlog is the total amount of oxygen to be delivered, and K is the constant proportional control factor combined with needed conversion factors (where the factor K is 0.05 in the exemplary configuration above).

During an individual inhalation, the algorithm is repeated for every predetermined time interval, and as the oxygen is actually delivered to the patient, the oxygen backlog is decreased by the amount of oxygen delivered to the patient for each predetermined time interval (146 in FIG. 9). Thus, the oxygen to be delivered, or the oxygen backlog, is decreased over the course of an inhalation. As the oxygen backlog is decreased, the flow of oxygen decreases, and over the course of the inhalation, the oxygen flow decreases and it is less likely that delivered oxygen will be left in the trachea at the end of inhalation.

Additionally, the processor may be programmed to integrate the total volume of oxygen inhaled over the course of a time period to alert the clinician if the total volume of oxygen inhaled is sufficient or not sufficient. For example, the processor may integrate the volume of oxygen that is actually delivered to the patient over the course of one minute. If there is insufficient oxygen delivered over the course of the one minute, the processor may notify the clinician of insufficient oxygen delivery through an alarm, such as an audible alarm and/or an on-screen message.

The oxygen delivery algorithm shown in FIG. 9 achieves the desired goals of increasing the amount of oxygen actually delivered to the patient, and decreasing the amount of wasted oxygen. For example, if the patient's breathing rate slows, there will be fewer predetermined time intervals wherein the breathing pressure value is less than zero (fewer inhalations). As the breathing rate slows, the oxygen backlog increases, because for every predetermined time interval, the algorithm is incrementing the amount of oxygen to be delivered, or the oxygen backlog. When a patient finally does inhale, the flow of oxygen will be proportionally increased based on the oxygen backlog. If the patient's breaths are weak, then a high flow of oxygen would cause the pressure to be positive, and oxygen would stop being delivered, thus reducing wasted oxygen.

While the invention has been described in particular with reference to certain illustrated configurations, such is not intended to limit the scope of the invention. The present invention may be embodied in other specific forms without departing from its spirit or essential characteristics. The described configurations are to be considered as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for identifying a source of oxygen delivery failure to a patient, the method comprising:
   detecting a patient's breathing pressure value to determine a plurality of breathing pressure values, and receiving the plurality of breathing pressure values at at least one processor;
   the at least one processor analyzing the plurality of breathing pressure values to determine if the patient is breathing or not breathing, and when the processor determines the patient is not breathing, the processor communicating with a flow valve to deliver a high-flow pulse of oxygen;
   measuring an oxygen flow rate through an oxygen delivery device to provide an oxygen flow rate value;
   receiving the oxygen flow rate value at the least one processor;
   the processor analyzing the oxygen flow rate value, and wherein the processor outputs an insufficient oxygen flow alarm when the oxygen flow rate is not greater than a predetermined threshold value;
   measuring a post-oxygen pulse breathing pressure value when the oxygen flow rate is less than the predetermined threshold value;
   receiving the post-oxygen pulse breathing pressure value at the at least one processor;
   the processor analyzing the post-oxygen pulse breathing pressure value, and wherein the processor outputs an apnea alarm when the post-oxygen pulse breathing pressure value is more negative than a predetermined threshold post-oxygen pulse breathing pressure value, and wherein the processor outputs an oxygen delivery device displacement alarm when the post-oxygen pulse breathing pressure values is equal to or less negative than predetermined threshold post-oxygen pulse breathing pressure value.

2. The method according to claim 1, wherein the step of measuring the oxygen flow rate through the oxygen delivery device comprises measuring the oxygen flow rate with a differential-pressure oxygen flow analyzer.

3. The method according to claim 1, wherein the step of measuring the oxygen flow rate through the oxygen delivery device comprises measuring the oxygen flow rate with a heated wire anemometer.

4. The method according to claim 1, wherein the steps of the processor outputting the apnea alarm and the oxygen delivery device displacement alarm include outputting an audible alarm.

5. The method according to claim 1, wherein the steps of the processor outputting an apnea alarm and an oxygen delivery device displacement alarm include outputting a visual alarm.

6. The method according to claim 1, wherein the high-flow pulse of oxygen is between 5 and 15 liters per minute.

7. The method according to claim 1, wherein the predetermined threshold value is between 2 and 7 liters per minute.

8. The method according to claim 1, wherein the predetermined threshold post-oxygen pulse breathing pressure value is +0.01 cm $H_2O$.

9. The method according to claim 1, wherein the at least one processor comprises an oxygen flow analyzer processor, and a second processor, the oxygen flow analyzer processor in communication with the oxygen flow analyzer and the second processor.

10. The method according to claim 1, wherein the at least one processor comprises a pressure sensor processor, and a second processor, the pressure sensor processor in communication with the pressure sensor and the second processor.

11. The method according to claim 1, wherein the at least one processor comprises an oxygen flow analyzer processor, a pressure sensor processor, and a third processor; the oxygen flow analyzer processor in communication with the oxygen flow analyzer and the third processor, and the pressure sensor processor in communication with the pressure sensor and the third processor.

12. The method according to claim 1, wherein the method further comprises the processor calculating a volume of oxygen inhaled by the patient during at least one predetermined time period, the processor
   analyzing the plurality of breathing pressure values to classify each as inhalation or expiration, and for a breathing pressure value classified as inhalation, calculating the volume of inhaled oxygen as the volume of oxygen due to the oxygen flow rate during the at least one predetermined time period.

13. An apparatus for identifying a source of oxygen delivery failure to a patient, the apparatus comprising:
   a pressure sensor to detect a patient's breathing pressure and provide a plurality of breathing pressure values, and provide a post-oxygen pulse breathing pressure value, the pressure sensor in communication with a processor;
   a variable flow valve to deliver a high-flow pulse of oxygen, the variable flow valve in communication with the processor;
   an oxygen flow analyzer to measure a parameter indicative of oxygen flow rate through an oxygen delivery device and provide an oxygen flow rate value, the oxygen flow analyzer in communication with the processor;
   the processor programmed to receive the plurality of breathing pressure values and to analyze the plurality of breathing pressure values to determine if the patient is breathing or not breathing, and the processor programmed to send a signal to the variable flow valve to open the valve to deliver the high-flow pulse of oxygen when the processor determines the patient is not breathing; and the processor programmed to receive the oxygen flow rate value and analyze the oxygen flow rate value to determine if the oxygen flow rate value is above a predetermined threshold value, and the processor further programmed to output an insufficient oxygen flow alarm when the oxygen flow rate value is below the predetermined threshold value;

the processor programmed to receive the post-oxygen pulse breathing pressure value and analyze the post-oxygen pulse breathing pressure value to determine if the post-oxygen pulse breathing pressure value is more negative than a predetermined threshold post-oxygen pulse breathing pressure value; and the processor programmed to output an apnea alarm if the post-oxygen pulse breathing pressure value is more negative than the predetermined threshold post-oxygen pulse breathing pressure value, and the processor programmed to output an oxygen delivery device displacement alarm when the post-oxygen pulse breathing pressure value is not more negative than the predetermined threshold post-oxygen pulse breathing pressure value.

14. The apparatus according to claim 13, wherein the oxygen flow analyzer comprises a differential-pressure oxygen flow analyzer.

15. The apparatus according to claim 13, wherein the variable flow valve comprises a proportional control valve.

16. The apparatus according to claim 13, wherein the high-flow pulse of oxygen comprises a pulse of oxygen of 5 to 15 liters per minute.

17. The apparatus according to claim 13, wherein the predetermined threshold value of the oxygen flow rate value is 2 to 10 liters per minute.

18. The apparatus according to claim 13, wherein the apnea alarm and the oxygen delivery device displacement alarm comprise an audible alarm.

19. The apparatus according to claim 13, wherein the apnea alarm and the oxygen delivery device displacement alarm comprise a visual alarm.

* * * * *